(12) United States Patent
Patel et al.

(10) Patent No.: US 9,827,171 B2
(45) Date of Patent: Nov. 28, 2017

(54) FILM FORMING CONTAINING COMPOSITIONS COMPRISING POLYVINYL ACETATE AND A PIGMENT

(71) Applicant: COLGATE-PALMOLIVE COMPANY, New York, NY (US)

(72) Inventors: Neeta A. Patel, Monmouth Junction, NJ (US); Gregory Szewczyk, Flemington, NJ (US); Suzanne Jogun, Wayne, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/107,577

(22) PCT Filed: Dec. 23, 2013

(86) PCT No.: PCT/US2013/077374
§ 371 (c)(1),
(2) Date: Jun. 23, 2016

(87) PCT Pub. No.: WO2015/099639
PCT Pub. Date: Jul. 2, 2015

(65) Prior Publication Data
US 2016/0317400 A1    Nov. 3, 2016

(51) Int. Cl.
*A61Q 11/00* (2006.01)
*A61K 47/38* (2006.01)
*A61K 8/02* (2006.01)
*A61K 8/73* (2006.01)
*A61K 8/81* (2006.01)
*A61K 8/04* (2006.01)
*A61K 8/34* (2006.01)
*A61K 8/49* (2006.01)

(52) U.S. Cl.
CPC ............ *A61K 8/0254* (2013.01); *A61K 8/042* (2013.01); *A61K 8/345* (2013.01); *A61K 8/4993* (2013.01); *A61K 8/731* (2013.01); *A61K 8/8135* (2013.01); *A61Q 11/00* (2013.01); *A61K 2800/262* (2013.01); *A61K 2800/43* (2013.01); *A61K 2800/45* (2013.01)

(58) Field of Classification Search
CPC ............. A61K 8/731; A61K 2800/262; A61K 8/0216; A61K 2800/56; A61K 8/0254; A61K 2800/43; A61K 8/042; A61K 47/38; A61Q 11/00
See application file for complete search history.

(56) References Cited

U.S. PATENT DOCUMENTS

| | | | | |
|---|---|---|---|---|
| 3,935,306 A | * | 1/1976 | Roberts | A61K 8/0275 424/49 |
| 8,540,823 B2 | | 9/2013 | Drehs et al. | |
| 2003/0194382 A1 | * | 10/2003 | Chang | A61K 8/0208 424/53 |
| 2008/0160056 A1 | * | 7/2008 | Boyd | A61K 8/042 424/401 |
| 2012/0070478 A1 | * | 3/2012 | Boyd | A61K 8/345 424/401 |
| 2014/0322140 A1 | | 10/2014 | Pan et al. | |

FOREIGN PATENT DOCUMENTS

| | | | | |
|---|---|---|---|---|
| WO | WO 2010146601 A1 | * | 12/2010 | ............. A61K 9/006 |
| WO | WO2011094497 A2 | | 8/2011 | |
| WO | WO 2012002946 A1 | * | 1/2012 | ............... A61K 8/02 |
| WO | WO2013039495 | | 3/2013 | |
| WO | WO2013096321 | | 6/2013 | |

OTHER PUBLICATIONS

Corresponding International Search Report and Written Opinion for PCT/US2013/077374 dated Apr. 17, 2014.
Makarov, 1979, "Sanitary rules for the production of basic lead-containing pigments," Deputy Chief of State Sanitary Doctor of the USSR, accessed from http://lawru.info/dok/1979/05/24/n118146.htm.

* cited by examiner

*Primary Examiner* — Tracy Liu

(57) ABSTRACT

Described herein are compositions comprising a film, wherein the film comprises a pigment, and is adapted to release the pigment at a specific point in time during use; and methods of making and using the same.

12 Claims, No Drawings

FILM FORMING CONTAINING COMPOSITIONS COMPRISING POLYVINYL ACETATE AND A PIGMENT

CROSS-REFERENCE TO RELATED PATENT APPLICATIONS

The present application is a U.S. national stage application under 35 U.S.C. §371 of PCT Application No. PCT/US2013/077374, filed Dec. 23, 2013, the entirety of which is incorporated herein by reference.

BACKGROUND

It is recommended that children should brush their teeth for at least 45-60 seconds, and adults for at least 90 to 120 seconds. Most people, especially children, do not brush their teeth for a sufficient period of time to obtain maximum benefit, and moreover have difficulty accurately estimating the time necessary to brush the teeth.

There is a need for toothpastes comprising films, which deliver a color change signal after brushing for appropriate period of time, and optionally deliver an active ingredient during the brushing period; thereby encouraging users to brush their teeth for a longer period of time.

Some toothpastes, containing films with pigments and, optionally, other actives, can release pigment and/or other actives prematurely, e.g., during storage, thereby compromising the color change signal and/or other beneficial properties. Thus there is a need for more stable toothpastes that contain films with pigments.

SUMMARY

In some embodiments, the present invention provides oral care compositions comprising films comprising a pigment, wherein the film has improved stability, in particular in formulations with a high water content, e.g., greater than about 20%, and/or a high glycerol content, e.g., greater than about 25%. The compositions of the invention are oral care compositions comprising color-changing films, which are attractive and stable in the formulation and provide a color change signal after a sufficient period of use. The oral compositions of the invention are stable upon storage, e.g., the pigment does not migrate or leak from the film into the carrier vehicle during storage, but is released upon introduction into the oral cavity to provide a visible signal, e.g, upon brushing.

The present inventors have developed compositions comprising films comprising a high concentration of pigment, which are stable in formulation, but are adapted to provide a color change after a sufficient period of brushing. The user would be instructed to continue brushing until the color change was observed, to help ensure that they have brushed for a sufficient period of time. One difficulty presented in formulating such a product is to prevent the release of pigment from the film or disintegration of the film with pigment during storage. This problem is particularly prevalent in high water content toothpastes or dentifrices, e.g., about 20% or greater water and/or high glycerol content, e.g., about 25% or greater glycerol. The present inventors have overcome the stability difficulties by use of a particular polymer matrix of which the film is comprised.

In accordance with the present invention there is provided an oral care composition such as a dentifrice comprising:

(i) flakes of a water dissolvable or soluble film (hereinafter sometimes referred to as "film flakes") comprised of
  (a) a mixture of a water soluble hydroxyalkyl cellulose polymer and polyvinyl acetate in the form of a single layer polymer matrix, and
  (b) a pigment entrained in the polymer matrix, and, optionally, other actives, and
(ii) an orally acceptable carrier vehicle,
wherein the composition comprises about 20 to up to 32% water and/or 25% or greater humectant such as glycerol.

In one embodiment of the invention there is provided an aesthetically decorative dentifrice having distributed throughout film flakes in which a decorative pigment is entrained in the film matrix, the dentifrice vehicle being substantially clear so that the aesthetically decorative effect can be viewed by the user.

In another embodiment other actives such as therapeutic and/or cosmetic agents, in addition to the pigment, are entrained in the film polymer matrix and/or the orally acceptable carrier vehicle.

The entrainment of pigment and, optionally, other therapeutic and cosmetic agents in the film flake matrix suspended in the orally acceptable carrier vehicle isolates these agents from interaction with reactive ingredients present in the orally acceptable carrier vehicle so that the film flake agents are maintained substantially separate from the reactive dentifrice ingredients in the orally acceptable carrier vehicle during manufacture and storage while subsequently being released from the film matrix when the dentifrice containing the film flakes is topically applied to the tooth surface as by tooth brushing generally one that is substantially water insoluble, for example a pigment, fragrance, flavor, topical anesthetic, or topical antibacterial agent.

Some embodiments of the present invention further provide a composition which is subjected to agitation and moisture during use, e.g., an oral care product which is applied by brushing or scrubbing, for example a toothpaste.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

The Film

The films of the present invention are formed from film forming polymers in the form of a polymer matrix comprised of hydroxyalkyl cellulose and polyvinyl acetate in which is entrained a pigment, and, optionally other agents such as a flavorant, a sweetener and/or a therapeutic agent such as an antibacterial agent or a breath freshening agent. The film matrix can further comprise water, additional film forming agents such as corn starch, e.g., Hi-Set C™ from National Starch., plasticizing agents, e.g., propylene glycol, surfactants, e.g., polysorbate 80, and emulsifying agents. The films of the invention are preferable single layer.

Preparation of Film Matrix

In preparing the film matrix according to the present invention the hydroxyalkyl cellulose, polyvinyl acetate, pigment, and optionally, flavor, sweetener and/or therapeutic agents and other film forming ingredients are dissolved in a compatible solvent to form a film forming composition. Compatible solvents include water, alcohols such as ethanol, ethyl acetate, acetone, and mixtures thereof. The film forming composition is cast on a releasable carrier and dried to form a sheet of film matrix material. The carrier material must have a surface tension which allows the film solution to spread evenly across the intended carrier width without soaking to form a destructive bond between the film carrier substrates. Examples of suitable carrier materials include glass, stainless steel, Teflon and polyethylene-impregnated paper. Drying of the film may be carried out at high temperature using a drying oven, drying terminal, vacuum drier, or any other suitable drying equipment which does not adversely affect the ingredients of which the film is composed.

The film thickness ranges in size from about 1 to 10 mils, in one embodiment about 1 to 5 mils, in another embodiment about 2 to 4 mils. The dried film of the present invention is then cut, punched or ground into flakes having a particle size of 10 to 100 mesh, or 20 to 60 mesh or 30 to 50 mesh.

If desired, additional stability can be provided to the shapes formed from the dried film, by applying to the film, before shaping into flakes, a protective barrier overcoat such as a food grade shellac or ethyl cellulose.

When the film is to be used for decorative effect, the film once formed is punched into various attractive shaped flakes such as hearts, stars, diamonds and circles. Optionally, the film can be ground into flakes using conventional grinding techniques known in the art. The film flakes are incorporated in the orally acceptable carrier vehicle of the present invention at a concentration of about 0.05 to 1.0% by weight and in one embodiment about 0.1 to about 0.5% by weight.

Film Forming Polymers

A major film forming agent used to prepare the film matrix of the present invention is a hydroxyalkyl cellulose such as hydroxypropylmethyl cellulose (HPMC), hydroxyethylpropyl cellulose, and hydroxybutylmethyl cellulose. The term "alkyl" in this context means $C_{1-4}$ alkyl.

Preferably the cellulose polymer is a low viscosity hydropropylmethyl cellulose polymer.

The hydroxyalkyl cellulose is incorporated in the film matrix in amounts ranging from about 10 to about 60% by weight and in one embodiment about 15 to about 40% by weight The other major film forming polymer used to prepare the film matrix of the present invention is polyvinyl acetate (PVAc). In certain embodiments, the amount of polyvinyl acetate is at least 1, 10, 20, 30, 40, 50, 60, 70, 80 or 90 weight % of the film matrix. Increasing polyvinyl acetate can lead to an increase in the stability of the flakes in the composition.

An exemplary film can be produced from a film composition containing a mixture of PVAc and HPMC. In one embodiment, the amount of PVAc is 1 to 99 weight % of the polymer system, and the HPMC is 99 to 1 weight % of the polymer system. As a desired embodiment, the film is produced from an aqueous polymer system such that a volatile or organic solvent is not utilized. For example, a suspension of PVAc is mixed with HPMC to form an aqueous mixture such that there is no volatile or organic solvent that needs to be removed. An example of a suitable PVAc suspension is commercially available from BASF under the trade name KOLLICOAT™ SR 30 D. HPMC is available commercially, for example, from the Dow Chemical Company under the trade designation Methocel™, including, for example, Methocel™ E5LV, Methocel™ E50, and Methocel™ K100. Methocel™ E5 LV is a USP grade, low viscosity HPMC having 28 to 30 (29.1) % methoxyl groups and 7 to 12 (9) % hydroxypropyl group substitution. As used herein, hydroxypropylmethylcellulose E5 refers to hydroxypropylmethylcellulose have a viscosity of about 5 (4 to 6) mPas (cps), and hydroxypropylmethylcellulose E50 refers to hydroxypropylmethyl cellulose have a viscosity of about 50 (40 to 60) mPas (cps). The viscosity for the hydroxypropylemethyl cellulose is measured in a 2 weight % solution in water at 20° C. with a Ubbelohde tube viscometer.

In one embodiment, the polymer system comprises E5 hydroxypropylmethyl cellulose and polyvinyl acetate. In another embodiment the polymer system comprises E5 hydroxypropylmethyl cellulose, E50 hydroxypropylmethyl cellulose and polyvinyl acetate. The following percentages are based on the total, active weight of the polymer system in the film. In one embodiment, the polymer system comprises about three times the amount of E5 hydroxypropylmethylcellulose by weight as the amount of polyvinyl acetate by weight. In one embodiment, the amount is about 76.9 weight % E5 hydroxypropylmethyl cellulose and about 23.1% polyvinyl acetate. In one embodiment, the polymer system comprises 60 to 85, 65 to 85, 70 to 85, 75 to 85, 60 to 80, 65 to 80, or 70 to 80 weight % hydroxypropylmethyl cellulose and 15 to 40, 15 to 35, 15 to 30, 20 to 40, 20 to 35, or 30 to 40 weight % polyvinyl acetate. In another embodiment, the polymer system comprises 70 to 85, 70 to 80, 75 to 85, or 75 to 80 weight % E5 hydroxypropylmethylcellulose and 15 to 30, 15 to 25, 20 to 30, or 20 to 25 weight % polyvinyl acetate. In another embodiment, the polymer system comprises 13 to 21, 14 to 19, or 15 to 19 weight % E50 hydroxypropylmethyl cellulose, 47 to 68, 50 to 65, or 52 to 63 weight % E5 hydroxypropylmethyl cellulose, and 15 to 35 or 18 to 32 weight % polyvinyl acetate. In another embodiment, the polymer system comprises about 18.75 weight % E50 hydroxypropylmethyl cellulose 62.5 weight % E5 hydroxypropylmethyl cellulose, and 18.75 weight % polyvinyl acetate. In another embodiment, the polymer system comprises about 15.8 weight % E50 hydroxypropylmethyl cellulose, about 52.6 weight % E5 hydroxypropylmethyl cellulose, and about 31.6 weight % polyvinyl acetate.

It is an advantage of the composition of the invention that the film does not require a polymer that functions as a mucoadhesive polymer, e.g., polymers containing acrylate repeating units such as Carbopol® polymers. The film of the invention also does not require starch.

Pigment

A pigment is generally understood to be a shade/material which is insoluble in the relevant medium, at the relevant temperature. This is in contrast to dyes which are soluble. In the context of this invention, the "relevant medium" is human saliva, the liquid medium in which the composition is used, at the temperature of the oral cavity during brushing of the teeth, i.e. up to 37° C. As a reasonable approximation, the relevant medium may be considered to be water and the relevant temperature to be 25° C. The pigments for use in the composition of the invention are those that will provide a visible signal to the user. Suitable pigments are red, green, yellow, blue, violet or combinations of these pigments, preferably one of those listed in the Colour Index International. These pigments are listed as pigment violet 1 through to pigment violet 56 and pigment blue 1 through 83. Examples of pigment violets are pigment violet 1, 1:1, 1:2, 2, 3, 5:1, 13, 19, 23, 25, 27, 31, 32, 37, 39, 42, 44 and 50.

Examples of pigment blues are pigment blue 1, 2, 9, 10, 14, 15, 15:1, 15:2, 15:3, 15:4, 15:6 16, 18, 19, 24:1, 25, 56, 60, 61, 62 and 66. Other suitable pigments are pigment ultramarine blue and ultramarine violet. In some embodiments the pigment can have a hue angle, h, in the CIELAB system of from 200 to 320 degrees. A detailed description of hue angle may be found on p57 of Colour Chemistry 3rd edition by H. Zollinger published by Wiley-VCH. While the preferred single pigments are blue or violet, the same effect may be achieved through mixing pigments outside of this h range; for example, such a hue angle may also be obtained by mixing a red and blue pigment to yield a blue or blue-violet shaded pigment. Typically, the pigment is Pigment Blue 15, more specifically Pigment Blue 15:1, 15:2, 15:3, 15:4, 15:5 or 15:6. Examples of red pigment include Red 30, Red 40, and the like. The amount of pigment in the oral composition typically is from 0.01 to 0.3%, more particularly from 0.02 to 0.1%, and more particularly from 0.03 to 0.08% by weight. The pigment may be uniformly spread throughout the composition or, it may be dispersed in a second phase such as a stripe or other coextruded second phase. Such "dual phase" compositions have the advantage that the phases may be differently colored, presenting a more visually attractive product to the consumer.

Water

The compositions of the invention have a high water content, i.e., about 20% or greater. Water content of the compositions are typically between about 20 and about 30%, in another embodiment about 22 to about 28%, said percentages being based on the total weight of the composition. Water, employed in the preparation of commercial oral compositions should be deionized and free of organic impurities. This amount of water includes the free water which is added plus that amount which is introduced with other materials such as with sorbitol or any components of the invention. Water can be present in the film flakes, orally acceptable carrier vehicle, or both. It has been discovered that certain films comprised of film forming polymers containing pigments are unstable upon storage in a carrier vehicle if the water content of the composition exceeds about 33% or about 32%. The compositions of the invention preferably contain water in an amount of about 20 to 32%, in another embodiment about 20 to about 31%, in another embodiment about 20 to about 30%.

Humectants

The compositions of the invention typically contain a humectant such as glycerol. The amount of humectant, e.g., glycerol, typically is about 25% or greater or about 30% or greater or about 35% or greater, but can be about 15% to about 70% in one embodiment or about 30% to about 65% in another embodiment, or about 25 to about 50% in another embodiment, or about 30 to 50% in another embodiment, or about 35 to about 50% in another embodiment, said percentages being based on the total weight of the oral composition. Humectants generally prevent the composition from hardening upon exposure to air. Certain humectants can also impart desirable sweetness or flavor to dentifrice compositions. Other suitable humectants include other edible polyhydric alcohols, sorbitol, xylitol, propylene glycol as well as other polyols and mixtures of these humectants. Mixtures of glycerine (glycerol) and sorbitol may be used in certain embodiments as the humectant component of the compositions herein. The humectant can be present in the film flakes, orally acceptable carrier vehicle or both.

Orally Acceptable Carrier Vehicle

The oral care compositions of the invention include a vehicle or base into which the film flakes are incorporated. Examples of orally acceptable carrier vehicles include carrier polymers, humectants, water, abrasives, foaming agents, anti-calculus agents, thickener silicas, and the like, or any combination of two or more thereof. The term "orally-acceptable" refers to a polymer or ingredient which can be used to apply to the oral cavity in a safe manner during normal use.

Carrier Polymers

Carrier polymers can comprise one or more anionic or nonionic polymers, and also may include additional polymers to adjust the viscosity of the formulation or enhance the solubility of other ingredients.

Suitable carrier polymers include polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Anionic polymers useful herein may enhance the effect of the water insoluble whitening complex, for example in an amount of from about 0.001 to about 5%, more particularly about 0.01 to 5%, more particularly about 0.05 to 4%, more particularly about 0.05 to 3% of the composition. Such agents are known generally for use in dentifrice, although not for this particular application, useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 300,000 to about 800,000. These copolymers are available for example as Gantrez®. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference. Another useful class of polymeric agents includes polyamino acids containing proportions of anionic surface-active amino acids such as aspartic acid, glutamic acid and phosphoserine, (in addition to the basic amino acid polymers), e.g. as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Hydroxyalkyl methyl cellulose may also be present in the non-film portion of the oral composition. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.05% to 5%, more particularly about 0.5 to 5% by weight of the total composition are used. Orally acceptable carrier polymers for use in the invention are typically water soluble. Suitable orally acceptable carrier polymers for use in the invention will generally dissolve or disperse in water at a temperature of 25° C. In addition to the hydroxyalkyl methyl cellulose in the film flakes, certain orally acceptable carrier polymers also are able to aid the deposition of the pigment onto the teeth such that tooth surface whiteness is enhanced.

The amount of orally acceptable carrier vehicle polymer in compositions of the invention, whether enhancers, deposition aids, thickeners or the like, or of a combination thereof, suitably ranges from about 0.001 to 10%, more particularly about 0.005 to 5%, more particularly about 1 to 5%, and more particularly about 1 to 3%.

Abrasives

The compositions of the invention, e.g. Composition 1 et seq. may comprise a calcium phosphate abrasive, e.g., tricalcium phosphate (Ca3(PO4)2), hydroxyapatite (Ca10(PO4)6(OH)2), or dicalcium phosphate dihydrate (CaHPO4*2H2O, also sometimes referred to herein as DiCal) or calcium pyrophosphate. The compositions may include one or more additional abrasives, for example silica abrasives such as precipitated silicas having a mean particle size of up to about 20 microns, such as Zeodent 115®, marketed by J. M. Huber. Other useful abrasives also include sodium metaphosphate, potassium metaphosphate, aluminum silicate, calcined alumina, bentonite or other siliceous materials, or combinations thereof. The silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, incorporated herein by reference.

In certain embodiments, abrasive materials useful in the practice of the oral care compositions in accordance with the invention include silica gels and precipitated amorphous silica having an oil absorption value of less than about 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns. Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present invention. The abrasive is present in the oral care composition of the present invention at a concentration of about 10 to about 60% by weight, in other embodiment about 20 to about 45% by weight, and in another embodiment about 30 to about 50% by weight.

Product Form

Examples of suitable product forms for compositions of the invention include dentifrices, mouthwashes, chewing gums and lozenges.

A type of product form of the present invention is a dentifrice. The term "dentifrice" generally denotes formulations which are used to clean the surfaces of the oral cavity. The dentifrice is an oral composition that is not intentionally swallowed for purposes of systemic administration of therapeutic agents, but is applied to the oral cavity, used to treat the oral cavity and then expectorated. Typically the dentifrice is used in conjunction with a cleaning implement such as a toothbrush, usually by applying it to the bristles of the toothbrush and then brushing the accessible surfaces of the oral cavity. Preferably the dentifrice is in the form of a paste or a gel (or a combination thereof).

Active Agents

The effective concentration of the active ingredients for optional use herein will depend on the particular agent and the delivery system used. It is understood that a toothpaste for example will typically be diluted with water upon use, while a mouth rinse typically will not be. Thus, an effective concentration of active in a toothpaste will ordinarily be 5-15× higher than required for a mouth rinse. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Active agents can include one or more of a fluoride ion source, an anti-calculus agent, an amino acid, a whitening agent, an antibacterial agent, and the like.

Arginine, where present, may be present at levels from, e.g., about 0.1 to about 20 wt % (expressed as weight of free base), e.g., about 0.1 to about 3 wt % for a mouthrinse, about 1 to about 10 wt % for a consumer toothpaste or about 7 to about 20 wt % for a professional or prescription treatment product. Fluoride where present may be present at levels of, e.g., about 25 to about 25,000 ppm, for example about 25 to about 250 ppm for a mouthrinse, about 750 to about 2,000 ppm for a consumer toothpaste, or about 2,000 to about 25,000 ppm for a professional or prescription treatment product.

Antibacterial agents may be included in the oral composition of the present invention and particularly noncationic halogenated diphenyl ethers agents which are desirable from considerations of effectiveness and safety such as 2',4,4' trichloro-2 hydroxy-diphenyl ether (Triclosan) and 2,2'-dihydroxy-5,5' dibromophenyl ether. The antibacterial agent, when present in the oral composition is present in concentrations of about 0.05 to about 2% by weight and preferably 0.1 to about 1% by weight. Levels of antibacterial agents will vary similarly, with levels used in toothpaste being e.g., about 5 to about 15 times greater than used in mouthrinse. For example, a triclosan mouthrinse may contain, e.g., about 0.03 wt % triclosan while a triclosan toothpaste may contain about 0.3 wt % triclosan.

Agents used to diminish teeth sensitivity such as potassium chloride, potassium nitrate and potassium citrate may also be included in oral compositions of the present invention at concentrations of about 0.1 to about 10% by weight.

Whitening Agents

Whitening agents which may be present in the oral composition include peroxides, metal chlorites, perborates, percarbonates, peroxyacids, persulfates, and combinations thereof. Suitable peroxide compounds include hydrogen peroxide, urea peroxide, calcium peroxide, and mixtures thereof. Suitable metal chlorites include calcium chlorite, barium chlorite, magnesium chlorite, lithium chlorite, sodium chlorite, and potassium chlorite.

Fluoride Ion Source

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al., U.S. Pat. No. 4,885,155, to Parran, Jr. et al. and U.S. Pat. No. 3,678,154, to Widder et al., incorporated herein by reference. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the invention may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions of the invention at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counter ion in the salt.

Foaming Agents

The oral care compositions of the invention also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present invention. The dosage of foaming agent in the oral care composition (i.e., a single dose) is about 0.01 to about 0.9% by weight, about 0.05 to about 0.5% by weight, and in another embodiment about 0.1 to about 0.2% by weight.

Anticalculus Agents

The oral composition can include at least one anticalculus composition, such as one or more of the anticalculus compositions recited in U.S. Pat. No. 5,292,526 titled "Antibacterial Anti-plaque Anticalculus Oral Composition," which is incorporated herein by reference. In various embodiments, the anti-calculus composition includes one or more polyphosphates. The anti-calculus composition can include at least one wholly or partially neutralized alkali metal or ammonium tripolyphosphate or hexametaphosphate salt present in the oral composition at an effective anti-calculus amount. The anti-calculus composition can also include at least one water soluble, linear, molecularly dehydrated polyphosphate salt effective in an anticalculus amount. The anti-calculus composition can also include a mixture of potassium and sodium salts at least one of which is present in an effective anti-calculus amount as a polyphosphate anti-calculus agent. The anti-calculus composition can also contain an effective anticalculus amount of linear molecularly dehydrated polyphosphate salt anti-calculus agent present in a mixture of sodium and potassium salts. Other useful anticalculus agents include polycarboxylate polymers and polyvinyl methyl ether/maleic anhydride (PVME/MA) copolymers, such as GANTREZ®.

Surfactants

The compositions useful in the invention may contain anionic and/or nonioinic surfactants, for example:

i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate, ii. higher alkyl sulfates, such as sodium lauryl sulfate, iii. higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example sodium laureth-2 sulfate $(CH_3(CH_2)10CH_2(OCH_2CH_2)_2OSO_3Na)$.

iv. higher alkyl aryl sulfonates such as sodium dodecyl benzene sulfonate (sodium lauryl benzene sulfonate)

v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., C6-30 alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used for a mouthwash are typically on the order of one tenth that used for a toothpaste. In one embodiment, the anionic surfactant is present in a toothpaste at from about 0.3% to about 4.5% by weight, e.g., about 1.5%.

Nonionic surfactants include nonanionic polyoxyethylene surfactants such as Polyoxamer 407, Steareth 30, Polysorbate 20, and PEG-40 castor oil and amphoteric surfactants such as cocamiopropyl betaine (tegobaine) and cocamidopropyl betaine lauryl glucoside condensation products of ethylene oxide with various hydrogen containing compounds that are reactive therewith and have long hydrophobic chains (e.g., aliphatic chains of about 12 to 20 carbon atoms), which condensation products ("ethoxamers") contain hydrophilic polyoxyehtylene moieties, such as condensation products of poly (ethylene oxide) with fatty acids, fatty alcohols, fatty amides and other fatty moieties, and with propylene oxide and polypropylene oxides (e.g., Pluronic® materials).

The compositions of the invention may optionally contain mixtures of surfactants, e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al., which are incorporated herein by reference. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. In a particular embodiment, the composition of the invention, e.g., Composition 1, et seq., comprises sodium lauryl sulfate.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

Flavoring Agents

The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.1 to about 5% by weight and about 0.5 to about 1.5% by weight. The dosage of flavoring agent in the individual oral care composition dosage (i.e., a single dose) is about 0.001 to 0.05% by weight and in another embodiment about 0.005 to about 0.015% by weight.

Other Optional Ingredients

In addition to the above-described components, the embodiments of this invention can contain a variety of optional dentifrice ingredients some of which are described below. Optional ingredients include, for example, but are not limited to, adhesives, sudsing agents, sweetening agents, and additional coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

In general, the various agents and materials described herein, e.g., fluoride ion source, antibacterials, flavoring agents, whitening agents, and the like, can be present in the film flakes, orally acceptable carrier vehicle, or both.

Unless otherwise specified, all percentages and amounts expressed herein and elsewhere in the specification should be understood to refer to percentages by weight. The amounts given are based on the active weight of the material. For convenience, components of the composition of invention are expressed in the singular; however it is to be understood that mixtures of components are encompassed by use of the singular expression, for example, "an orally acceptable carrier polymer" may include mixtures of two or more polymers described herein.

The invention also includes a method for temporarily whitening teeth comprising administering an effective amount of the composition of the invention to the oral cavity of a subject in need thereof. The whitening effect of the composition is considered temporary in that it's whitening effect will noticeably diminish within about two weeks after application if not additionally treated.

Some embodiments of the present invention provide an oral care composition (Composition 1) comprising:
(i) flakes of a water dissolvable or soluble film comprised of
  (a) a mixture of a water soluble hydroxyalkyl cellulose polymer and polyvinyl acetate in the form of a single layer polymer matrix, and
  (b) a pigment entrained in the polymer matrix, and, optionally, other actives, and
(ii) an orally acceptable carrier vehicle,
wherein the composition comprises between about 20 and up to 32% water and 25% or greater glycerol, for example:
  1.1. Composition 1 wherein the hydroxyalkyl cellulose is hydroxypropylmethyl cellulose.
  1.2. Any of the foregoing compositions wherein the film does not contain a polymer that functions as a mucoadhesive polymer, e.g., polymers containing acrylate repeating units.
  1.3. Any of the foregoing compositions wherein the film does not contain starch.
  1.4. Any of the foregoing compositions wherein the amount of water is about 22 to about 28%;

1.5. Any of the foregoing compositions wherein the amount of glycerol is about 25 to about 50%;
1.6. Any of the foregoing compositions wherein the film further comprises a plasticizer, e.g, a polyalcohol, e.g., sorbitol, propylene glycol, glycerol, or low molecular weight polyethylene glycol, e.g., PEG 200;
1.7. Any of the foregoing compositions wherein the film further comprises propylene glycol, e.g., in an amount effective to provide plasticity to the film, e.g., about 20-30% by dry weight of the film;
1.8. Any of the foregoing compositions wherein the film further comprises a non-ionic surfactant or emulsifier, e.g., a polysorbate, e.g., polysorbate 80 (also known as polyoxyethylene(20) sorbitan monooleate, available commercially e.g., as Tween® 80), e.g., in an amount of about 1-5% by dry weight of the film;
1.9. Any of the foregoing compositions wherein the pigment is a red pigment, for example D&C Red 30, a green pigment, for example Pigment Green 7, a blue pigment, for example a phthalocyanine, for example Pigment Blue 15:

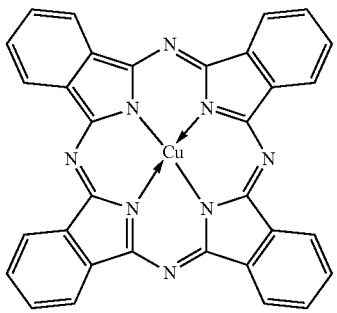

or a combination of any of these pigments;
1.10. Any of the foregoing compositions wherein the film is substantially dissolved after a period of greater than 30 seconds and less than 180 seconds of brushing, scrubbing or agitation in the oral cavity or on the skin in the presence of water;
1.11. Any of the foregoing compositions wherein the average thickness of the film is 1-4 mil, e.g. 1.5-3 mil, e.g. about 1.5 mil, about 2 mil or about 3 mil;
1.12. Any of the foregoing compositions wherein the film comprises, by dry weight of the film, 20-60% hydroxypropylmethyl cellulose, 30-50% polyvinyl acetate; 10-30% propylene glycol; 1-5% polysorbate 80; and 15-30% or 15-55% pigment;
1.13. Any of the foregoing compositions wherein the film flakes comprise 0.1-10%, or 0.2-0.5% or about 0.3% of the composition;
1.14. Any of the foregoing compositions wherein the film additionally comprises flavors, fragrances, antibacterial agents, anesthetic agents or combinations thereof;
1.15. Any of the foregoing compositions wherein the films flakes have a particle size of 10 to 100 mesh, 20-60 mesh and 30-50 mesh;
1.16. Any of the foregoing compositions wherein the orally acceptable carrier vehicle comprises a synthetic anionic polymeric polycarboxylate;
1.17. Any of the foregoing compositions wherein the orally acceptable carrier vehicle is a 1:4 to 4:1 copolymers of maleic anhydride or acid with another polymerizable ethylenically unsaturated monomer;
1.18. Any of the foregoing compositions wherein the orally acceptable carrier vehicle polymer is a methyl vinyl ether/maleic anhydride copolymer having an average molecular weight (M.W.) of about 30,000 to about 1,000,000, e.g. about 300,000 to about 800,000;
1.19. Any of the foregoing compositions wherein the orally acceptable carrier vehicle polymer is about 1-5%, e.g., about 2% of the weight of the composition.
1.20. Any of the foregoing compositions further comprising an effective amount of fluoride, e.g., wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof;
1.21. Any of the foregoing compositions comprising L-arginine in free or orally acceptable salt form;
1.22. Any of the foregoing compositions comprising buffering agents, e.g., sodium phosphate buffer (e.g., sodium phosphate monobasic and disodium phosphate)
1.23. Any of the foregoing compositions comprising an additional humectant, e.g., selected from, sorbitol, propylene glycol, polyethylene glycol, xylitol, and mixtures thereof;
1.24. Any of the foregoing compositions further comprising an abrasive or particulate;
1.25. The foregoing composition wherein the abrasive or particulate is selected from sodium bicarbonate, calcium phosphate (e.g., dicalcium phosphate dihydrate), calcium sulfate, precipitated calcium carbonate, silica (e.g., hydrated silica), iron oxide, aluminum oxide, perlite, plastic particles, e.g., polyethylene, and combinations thereof;
1.26. Any of the foregoing compositions comprising an abrasive in an amount of about 15 wt. % to about 70 wt. % of the total composition weight;
1.27. Any of the foregoing compositions comprising one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof, e.g. in an amount of from about 0.3% to about 4.5% by weight;
1.28. Any of the foregoing compositions further comprising a viscosity modifying amount of one or more polymers selected from polyethylene glycols, polysaccharides (e.g., cellulose derivatives, for example carboxymethyl cellulose, polysaccharide gums, for example xanthan gum or carrageenan gum), and combinations thereof;
1.29. Any of the foregoing compositions further comprising flavoring and/or fragrance;
1.30. Any of the foregoing compositions comprising one or more antibacterial agents, for example comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride;

1.31. Any of the foregoing compositions comprising a whitening agent, e.g., a selected from the group consisting of peroxides, metal chlorites, perborates, percarbonates, peroxyacids, hypochlorites, and combinations thereof;

1.32. Any of the foregoing compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);

1.33. Any of the foregoing compositions further comprising a source of calcium and phosphate selected from (i) calcium-glass complexes, e.g., calcium sodium phosphosilicates, and (ii) calcium-protein complexes, e.g., casein phosphopeptide-amorphous calcium phosphate;

1.34. Any of the foregoing compositions further comprising a soluble calcium salt, e.g., selected from calcium sulfate, calcium chloride, calcium nitrate, calcium acetate, calcium lactate, and combinations thereof;

1.35. Any of the foregoing compositions further comprising a physiologically or orally acceptable potassium salt, e.g., potassium nitrate or potassium chloride, in an amount effective to reduce dentinal sensitivity;

1.36. Any of the foregoing compositions further comprising a breath freshener, fragrance or flavoring;

1.37. Any of the foregoing compositions in the form of a dentifrice, for example a toothpaste, e.g., a clear gel or opaque toothpaste;

1.38. Any of the foregoing compositions in the form of a clear gel or opaque toothpaste and the pigment is released upon dissolution of the film thereby changing the color of the toothpaste after brushing for a period of 30-180 seconds, e.g., about 45-60 seconds in a toothpaste for use by a child or about 90-120 seconds in a toothpaste for use by an adult, thereby releasing the pigment and providing a color signal to the user of adequate brushing;

The invention further provides a method of cleaning the teeth comprising brushing with a toothpaste comprising an orally acceptable dissolvable film of a hydroxyalkyl cellulose and PVAc having entrained therein a pigment (e.g., Composition 1 et seq.), wherein brushing is continued until the film disintegrates and the pigment provides a color signal to the user of adequate brushing, for example, wherein the brushing time before the film matrix dissolves is between 30 and 180 seconds, e.g., about 45-60 seconds for a toothpaste for use by a child and about 90-120 seconds for a toothpaste for use by an adult.

In some embodiments, the composition is a clear gel toothpaste; wherein the pigment is released from the first film after brushing for a period of 30 to 120 seconds. In some embodiments, the pigment is released from the first film after brushing for a period of 60 seconds. In some embodiments, the pigment is released from the first film after brushing for a period of 90 seconds. In some embodiments, the pigment is released from the first film after brushing for a period of 120 seconds.

The invention further provides a method of cleaning the teeth, removing plaque, treating halitosis, or treating gingivitis comprising brushing the teeth with Composition 1, et seq.

In some embodiments, the film is substantially dissolved after a period of greater than 30 seconds and less than 180 seconds of brushing, scrubbing or agitation in the presence of water.

In some embodiments, substantially all of the pigment is released from the first film at the same point in time.

In some embodiments the composition is stable, i.e., no visible pigment is observed in the carrier vehicle, for a period of 1 month or 2 months, or 3 months, or 6 months, or 1 year or 2 years upon storage at about room temperature.

Yet other embodiments provide a method of cleaning the teeth comprising brushing with a toothpaste according to Composition 1 et seq., wherein brushing is continued until the film releases substantially all of the pigment; thereby providing a color signal to the user of adequate brushing.

In some embodiments, substantially all of the pigment is released at one time. As used herein, the term "substantially all" refers to greater than 90% of the total amount of pigment contained in the film.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight.

EXAMPLES

Example 1

Film Making Procedure

Approximately fifty percent of the required film formula water is weighed out and heated as necessary depending on the polymer type. Polymers (HPMC, MC, etc) are slowly added to the water under mixing conditions and the polymers are allowed to disperse and hydrate for 10-15 minutes. Additional water up to the full amount is added until the slurry has the consistency of honey. Plasticizers and surfactants should then be added while mixing and allowed to mix for 5 minutes. Other particles such as pigments, etc. should then be added to the mixture and allowed to mix for 10 additional minutes. The slurry should then be de-aerated. Films can then be cast and dried from the slurry to the desired thickness typically 1-10 mils.

Example 2

Dissolution Test 1000 mL of cold water is placed into glass vessel with approximate dimensions of 9×13 inches. A 1×1 inch swatch of film is cut and floated on the surface of the water using forceps. The film should lay flat on the surface of the water. If the film curls a new container of water along with a new film swatch should be obtained. The time for the film to completely dissolve is recorded as dissolution time. The test should be repeated 3 times. Results are in Table 1.

TABLE 1

Poly Vinyl acetate film formula composition. Dissolution time in water

| | Film Formula | | | | | |
|---|---|---|---|---|---|---|
| | A | | B | | C | |
| Ingredients | Wt % | Wt % of Solids | Wt % | Wt % of Solids | Wt % | Wt % of Solids |
| Water | 72.00 | | 71.97 | | 72.00 | |
| Methocel E5 | 7.00 | 25.00 | 9.00 | 32.11 | 5.00 | 17.86 |
| Methocel E50 | 3.00 | 10.71 | 1.00 | 3.57 | 5.00 | 17.86 |
| Kollicoat SR30D, 30% active emulsion | 8.30 | 29.64 | 8.33 | 29.72 | 8.30 | 29.64 |
| Blue Pigment | 3.00 | 10.71 | 3.00 | 10.70 | 3.00 | 10.71 |
| Propylene Glycol | 6.20 | 22.14 | 6.20 | 22.12 | 6.20 | 22.14 |
| Tween 80 | 0.50 | 1.79 | 0.50 | 1.78 | 0.50 | 1.79 |
| Total | 100.00 | 100.00 | 100.00 | 100.00 | 100.00 | 100.00 |
| Film Dissolution Time, seconds | | 120 | | 180 | | 210 |

| | Film Formula | | | | | |
|---|---|---|---|---|---|---|
| | D | | E | | F | |
| Ingredients | Wt % | Wt % of Solids | Wt % | Wt % of Solids | Wt % | Wt % of Solids |
| Water | 67.70 | | 66.70 | | 63.70 | |
| Methocel E5 | 7.00 | 21.67 | 5.00 | 15.02 | 10.00 | 27.55 |
| Methocel E50 | 3.00 | 9.29 | 2.00 | 6.01 | 0.00 | 0.00 |
| Kollicoat SR30D, 30% active emulsion | 12.60 | 39.01 | 16.60 | 49.85 | 16.60 | 45.73 |
| Blue Pigment | 3.00 | 9.29 | 3.00 | 9.01 | 3.00 | 8.26 |
| Propylene Glycol | 6.20 | 19.20 | 6.20 | 18.62 | 6.20 | 17.08 |
| Tween 80 | 0.50 | 1.55 | 0.50 | 1.50 | 0.50 | 1.38 |
| Total | 100.00 | 100.00 | 100.00 | 100.00 | 100.00 | 100.00 |
| Film Dissolution Time, seconds | | 95 | | 150 | | Insoluble |

Example 3

Stability Test:

Stability is assessed visually through the use of a liquid toothpaste or the gel phase portion of a toothpaste where clarity is high. A high clarity gel phase of the above formulations was used for stability assessment where the silica portion which creates the opaque quality of a paste is removed. Ground film is added to the gel and permitted to age for a minimum of 24 hours and up to 3 months at room temperature. The results are in Table 2. The unstable option C showed immediate swelling of the film which worsened during the initial 24 hour period. The unstable film pieces double or triple in size as they swell and the pigment contained in the film begins to bleed and spread outward from the films. In contrast to this stable films such as A and B show no evidence of swelling of the film particle size throughout the 3 month period, and there is no evidence of blue colored bleeding into the gel.

TABLE 2

Insoluble Film stability tested in Toothpaste formula composition

| | Option A | | Option B | | Option C | |
|---|---|---|---|---|---|---|
| Ingredients | Gel phase | Tooth Paste | Gel phase | Tooth Paste | Gel phase | Tooth Paste |
| WATER | 7.3 | 7.3 | 12.30 | 12.30 | 17.3 | 17.3 |
| SODIUM FLUORIDE | 0.24 | 0.24 | 0.24 | 0.24 | 0.24 | 0.24 |
| SODIUM SACCHARIN | 0.30 | 0.30 | 0.30 | 0.30 | 0.30 | 0.30 |
| SODIUM CMC | 0.00 | 0.00 | 0.00 | 0.00 | 0.00 | 0.00 |
| XANTHAN GUM | 0.50 | 0.50 | 0.50 | 0.50 | 0.50 | 0.50 |
| IOTA CARRAGEENAN | 0.50 | 0.50 | 0.50 | 0.50 | 0.50 | 0.50 |
| GLYCERIN | 34.29 | 34.29 | 29.29 | 29.29 | 24.29 | 24.29 |
| SORBITOL | 18.00 | 18.00 | 18.00 | 18.00 | 18.00 | 18.00 |
| PROPYLENE GLYCOL | 0.50 | 0.50 | 0.50 | 0.50 | 0.50 | 0.50 |
| GANTREZ | 11.82 | 11.82 | 11.82 | 11.82 | 11.82 | 11.82 |
| NaOH, 50% SOLU | 1.20 | 1.20 | 1.20 | 1.20 | 1.20 | 1.20 |
| TITANIUM DIOXIDE | | 0.10 | | 0.10 | | 0.10 |
| ZEO 105 | | 10.00 | | 10.00 | | 10.00 |
| ZEO 114 | | 8.50 | | 8.50 | | 8.50 |
| ZEO165 | | 3.00 | | 3.00 | | 3.00 |
| SLS | | 1.75 | | 1.75 | | 1.75 |
| TRICLOSAN | | 0.30 | | 0.30 | | 0.30 |
| MICA | | 0.50 | | 0.50 | | 0.50 |
| E5/Kollicoat SR30D, 10/16.6 | 0.20 | 0.20 | 0.20 | 0.20 | 0.20 | 0.20 |
| COOLEST CRYSTAL MINT | | 1.00 | | 1.00 | | 1.00 |
| Total | | 100.00 | | 100.00 | | 100.00 |
| Targeted Total Water amount | 23% | 23% | 28% | 28% | 33% | 33% |
| formula calculate Total water, % | 22.6 | 22.6 | 27.6 | 27.6 | 32.6 | 32.6 |
| Film stability | | Stable | | Stable | | Not stable |

Example 4

Stability Comparison

E5 films which show water solubility are mixed into a toothpaste and demonstrate complete breakdown within a 24 hour period. These films are put into a toothpaste that has a water content at 27% However, when blending two HPMC polymers along with PVA the resulting film has stability in toothpaste formula up to 27% water content. The two HPMC used are E5 a hydrophilic polymer and a more hydrophobic E50 polymer. The evaluation of the blend of three polymers demonstrates no swelling or bleeding into the surrounding paste through three months at Room Temperature

Example 5

In Vitro Brushing Test

Brushing machine (Kal Tech Corp.) parameters were set to mimic brushing at a speed of 188 strokes/min. with a weight loading of 465 g. 2 g of test product was placed onto the brush head and mounted in the machine. 6 grams of water was added to the brushing well and the machine was set for a 2 minutes brushing interval. Aliquots can be taken throughout the brushing cycle to obtain a rate of color release (film breakdown). Two minutes are used for the endpoint of targeted brushing for adults. Color measurements are obtained by using a spectrophotometer capable of measuring on the L, a, b scale, where the delta E is calculated as a summation of the L,a,b initial versus final. The test is repeated three times and the average is reported. The results are in the following table:

|  | PVA film with HPMC in 27% aqueous toothpaste | HPMC film (no PVA) in 20% aqueous toothpaste |
| --- | --- | --- |
| Delta E | 25.24 | 33.63 |

CONCLUSION

The more water stable PVA film is able to release sufficient color for a measurable and visually noticeable color change. It is important to note that while the film is more water stable it still releases color during brushing on a similar scale to conventional HPMC based films.

The invention claimed is:

1. An oral care composition comprising:
   (i) flakes of a water soluble or dissolvable single layer film comprising
      (a) film forming polymers in the form of a single layer polymer matrix comprising hydroxyalkyl cellulose and polyvinyl acetate; and
      (b) a pigment entrained in the polymer matrix, and
   (ii) an orally acceptable carrier vehicle,
   wherein the composition comprises between about 20 and up to 32% water;
   and wherein the composition comprises between about 25 and 50% glycerol.

2. The composition of claim 1 wherein the hydroxyalkyl cellulose is hydroxypropylmethyl cellulose.

3. The composition according to claim 1, wherein the film further comprises a plasticizer selected from sorbitol, propylene glycol, and polyethylene glycol.

4. The composition according to claim 1, wherein the film comprises a polysorbate.

5. The composition according to claim 1, wherein the film is dissolved after a period of greater than 30 seconds and less than 180 seconds of brushing, scrubbing or agitation in the presence of water.

6. The composition according to claim 1 wherein the average thickness of the film is 1.5-3 mil.

7. The composition according to claim 1 wherein the film forming polymers comprise hydroxypropylmethyl cellulose E5, hydroxypropylmethyl cellulose E50, and polyvinyl acetate.

8. The composition according to claim 1, comprising, by dry weight of the film, 20-60% of hydroxypropylmethyl cellulose, 30-50% polyvinyl acetate; 10-30% propylene glycol; 1-5% polysorbate 80; and 15-30% pigment.

9. The composition according to claim 1 which is stable upon storage at about room temperature for 1 month, 2, months, 3 months, 6 months, 1 year or 2 years.

10. The composition of claim 1, which comprises a clear gel toothpaste, wherein the pigment is released from said first film after brushing for a period of 30 to 120 seconds.

11. The composition of claim 1 comprising 22 to 28% of water.

12. A method of cleaning the teeth comprising brushing with a composition according to claim 1, wherein brushing is continued until the film releases substantially all of the pigment; thereby providing a color signal to the user of adequate brushing.

* * * * *